United States Patent
Wang-Lee

[19]
[11] Patent Number: 6,021,520
[45] Date of Patent: Feb. 8, 2000

[54] EYESHIELD FOR A WELDER'S MASK

[76] Inventor: Min-Young Wang-Lee, No. 473, Chung-Shan S. Rd., Yung-Kang City, Tainan Hsien, Taiwan

[21] Appl. No.: 09/296,114

[22] Filed: Apr. 21, 1999

[51] Int. Cl.⁷ .................................................. A61F 9/06
[52] U.S. Cl. ..................................... 2/8; 359/361; 349/14
[58] Field of Search ........................... 2/8, 432; 219/147; 359/350, 361; 349/104, 105, 193, 195, 14

[56] References Cited

U.S. PATENT DOCUMENTS

| | | | |
|---|---|---|---|
| 4,071,912 | 2/1978 | Budmiger | 2/8 |
| 4,155,122 | 5/1979 | Budmiger | 2/8 |
| 4,637,678 | 1/1987 | Moss et al. | 350/3.7 |
| 4,878,748 | 11/1989 | Johansen et al. | 351/44 |
| 5,519,522 | 5/1996 | Fergason | 359/66 |

*Primary Examiner*—Michael A. Neas
*Attorney, Agent, or Firm*—Ladas & Parry

[57] ABSTRACT

A welder's eyeshield includes a helmet having a face portion with a lens window provided thereon, a liquid crystal assembly mounted on the lens window, an optical filter juxtaposed with the liquid crystal assembly on the lens window, the optical filter being made of a plastic material compounded with a dye material for attenuating infrared and ultraviolet light, and a control circuit electrically connected to the liquid crystal assembly for controlling light transmissivity of the liquid crystal assembly.

3 Claims, 2 Drawing Sheets

EYESHIELD FOR A WELDER'S MASK

BACKGROUND OF THE INVENTION

1. Field of the Invention

The present invention relates to a welder's eyeshield, more particularly to a welder's eyeshield with an optical filter for attenuating infrared and ultraviolet light.

2. Description of the Related Art

An eyeshield mask is generally used for protecting the wearer's eyes from extremely bright light such as light emitted during welding or the like. Traditional eyeshield masks include a headpiece for covering the wearer's face, and a lens window disposed on a center portion of the headpiece. A dark-colored lens filter having low light transmissivity is mounted on the lens window for protecting the wearer's eyes from direct exposure to harmful light. However, because the light transmissivity of the lens filter employed in the conventional eyeshield mask is relatively low and fixed, the conventional eyeshield mask can only be used under bright ambient light conditions. When the ambient light is weak, the wearer normally has to remove the mask so as not to impair his seeing ability. In this case, the need to put on and take off the mask frequently during welding inconveniences the wearer.

U.S. Pat. No. 4,155,122 disclosed an eyeshield (see FIGS. 1 and 2) having a helmet 1 with a window 10 provided thereon. A liquid crystal assembly 11 and an optical filter lens 12 are juxtaposed on the window 10. The light transmissivity of the liquid crystal assembly 11 can be adjusted by a control circuit 13 connected to the liquid crystal assembly 11, thereby allowing this type of eyeshield to overcome the disadvantage described above. However, manufacturing of this type of eyeshield is laborious and incurs a higher rate of defects. This is due to the fact that the substrate used for the optical filter lens 12 is made of glass, which is fragile and tends to break during processing. Moreover, the surface of the glass is coated with a layer of reflective film 14 by vacuum electro-plating. The reflective film 14, which is merely adhered on the surface of the glass substrate, tends to be scratched off, thereby resulting in the loss of its effect on filtering light. In addition, the film 14 tends to be influenced by the ambient environment, such as temperature or moisture that is conducive to mold growth which can also cause the film 14 to lose its effect on filtering light too.

SUMMARY OF THE INVENTION

Therefore, it is an object of the present invention to provide a welder's eyeshield that is capable of overcoming the advantages described above.

According to the present invention, a welder's eyeshield comprises: a helmet including a face portion having a lens window provided thereon; a liquid crystal assembly mounted on the lens window; an optical filter juxtaposed with the liquid crystal assembly on the lens window, the optical filter being made of a plastic material compounded with a dye material for attenuating infrared and ultraviolet light; and a control circuit electrically connected to the liquid crystal assembly for controlling light transmissivity of the liquid crystal assembly.

BRIEF DESCRIPTION OF THE DRAWINGS

In drawings which illustrate an embodiment of the invention.

DETAILED DESCRIPTION OF THE INVENTION

Figure 2:
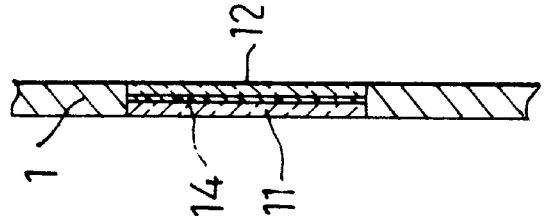
FIG. 2 is a cross-sectional view of the optical filter lens and the liquid crystal assembly of the welder's eyeshield of FIG. 1.
Figure 1:
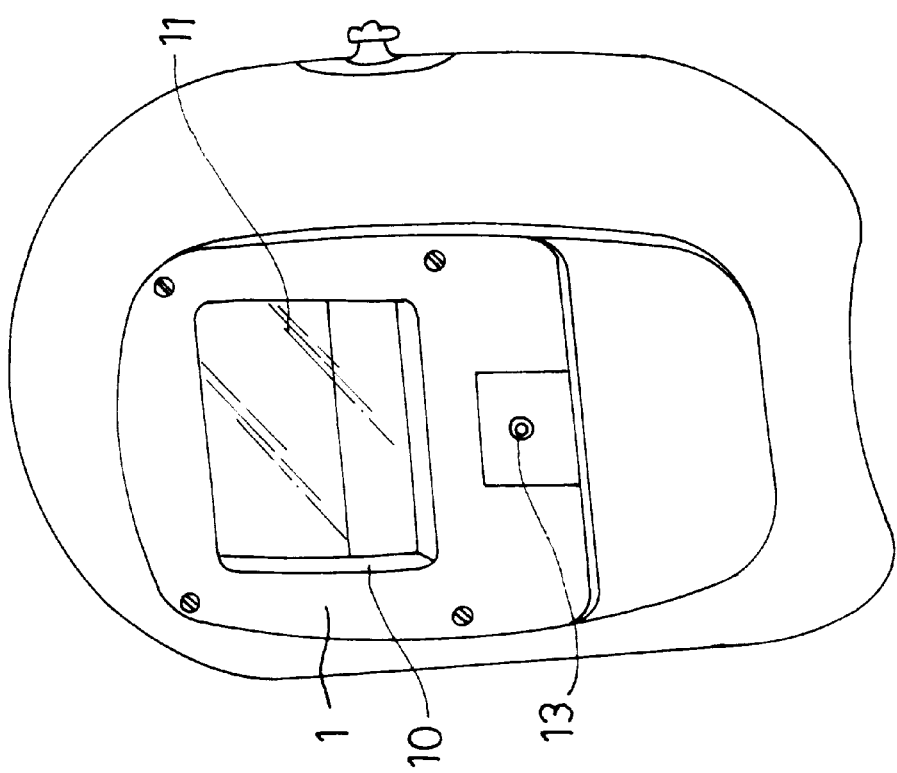
FIG. 1 is a perspective view of a conventional welder's eyeshield.
Figure 4:
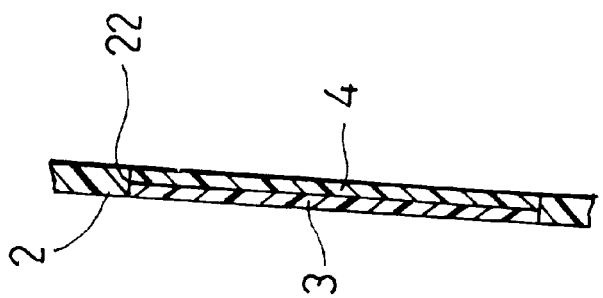
FIG. 4 is a cross-sectional view of the optical filter lens and the liquid crystal assembly of the emboiment.
Figure 3:
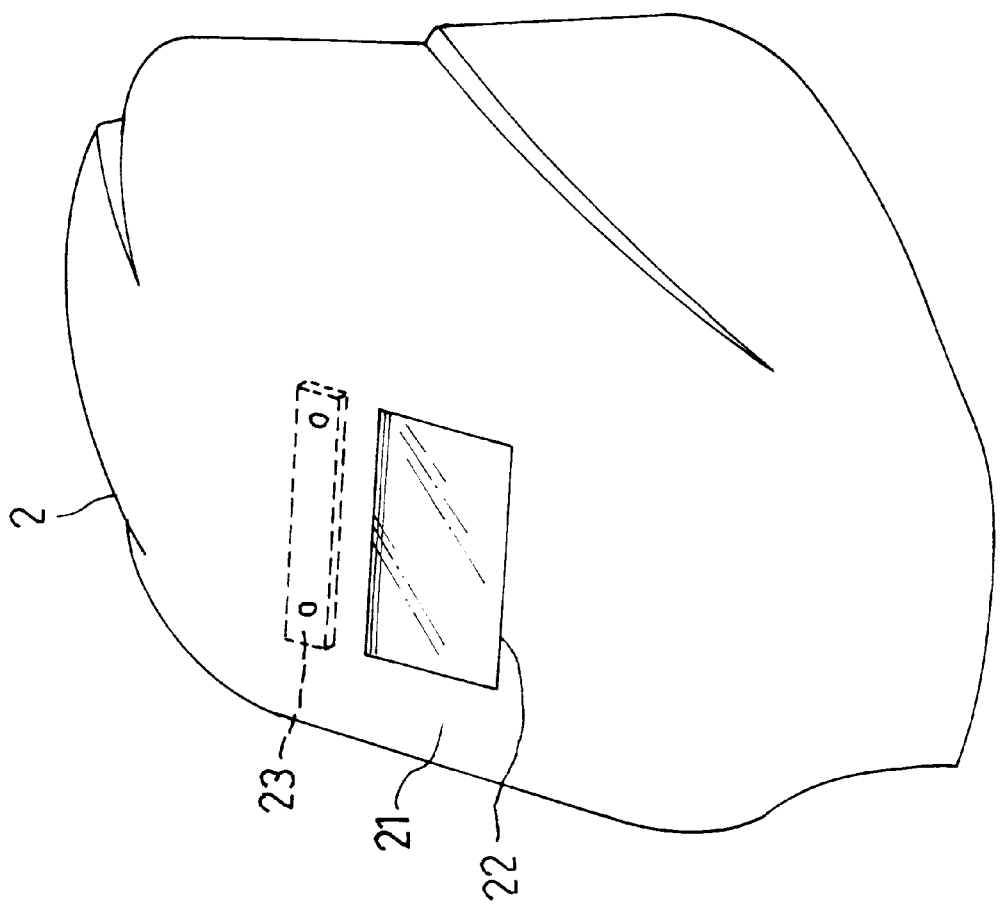
FIG. 3 is a perspective view of a welder's eyeshield embodying this invention.

FIGS. 3 and 4 illustrate a helmet 2 embodying this invention. The helmet 2 is used to protect the eyes of a welder, and includes a face portion 21 to confront the welder's face. A lens window 22 is provided on the face portion 21.

A liquid crystal assembly 3 which is generally rectangular in shape, is mounted on the lens window 22. A control circuit 23 is mounted on the helmet 2 and is electrically connected to the liquid crystal assembly 3 for automatically adjusting the light transmissivity of the liquid crystal assembly 3 according to the ambient light conditions.

An optical filter 4, which is generally rectangular in shape, is juxtaposed with the liquid crystal assembly 3 on the lens window 22. The optical filter 4 is made of a transparent plastic material compounded with a dye material. The plastic material used for the optical filter 4 of this invention is preferably selected from the group consisting of acrylic resin and polycarbonate. The dye materials used for the optical filter 4 are those that permit the optical filter 4 to filter out infrared and ultraviolet light. The optical filter 4 of this invention is made into plate by extrusion of melted plastic pre-compounded with the dye material.

When in use, the helmet 2 permits the welder to see through the liquid crystal assembly 3 and the optical filter 4. The optical filter 4 is disposed on an outer side of the liquid crystal assembly 3. Thus, infrared and ultraviolet light components of the ambient light can be filtered out before reaching the liquid crystal assembly 3. The transmissivity of the liquid crystal assembly 3 is automatically reduced by the control circuit 23 when the ambient light is too bright for the welder, and is increased when the ambient light is too weak.

One advantage of the optical filter 4 as compared to that used in U.S. Pat. No. 4,155,122 is that the substrate of the optical filter 4 of this invention is made by extrusion of melted plastic pre-compounded the dye material. Therefore, the problems, such as the breakage during processing and higher rate of defects, can be dramatically reduced in the present invention.

Another advantage according to present invention is that the dye material is uniformly dispersed inside the plastic material. Therefore, the optical filter 4 will not be influenced by the ambient conditions, such as the growth of mold, and its light transmissivity will not be affected by scratches on its surface.

The invention shall not be limited by the embodiment described above, which are exemplary and which can be modified in various ways within the scope of protection defined by the appended patent claims.

I claim:

1. A welder's eyeshield comprising:

a helmet including a face portion having a lens window provided thereon;

a liquid crystal assembly mounted on said lens window;

an optical filter juxtaposed with said liquid crystal assembly on said lens window, said optical filter being made of a plastic material compounded with a dye material for attenuating infrared and ultraviolet light; and a control circuit electrically connected to said liquid crystal assembly for controlling light transmissivity of said liquid crystal assembly.

2. The welder's eyeshield of claim 1, wherein said plastic material is made of acrylic resin.

3. The welder's eyeshield of claim 1, wherein said plastic material is made of polycarbonate.

* * * * *